United States Patent [19]

Owens et al.

[11] Patent Number: 4,480,040
[45] Date of Patent: Oct. 30, 1984

[54] SENSITIVE AND RAPID DIAGNOSIS OF VIROID DISEASES AND VIRUSES

[75] Inventors: Robert A. Owens; Theodor O. Diener, both of Beltsville, Md.

[73] Assignee: The United States of America as represented by the Secretary of Agriculture, Washington, D.C.

[21] Appl. No.: 327,296

[22] Filed: Dec. 3, 1981

[51] Int. Cl.³ ................. G01N 33/50; C12N 15/00
[52] U.S. Cl. ........................ 436/504; 436/63; 436/64; 436/94; 436/804; 436/813; 436/815; 435/6; 435/172.3; 435/91; 435/270; 935/78; 935/64; 935/6; 935/29; 935/73
[58] Field of Search ............... 424/1, 1.1, 195; 23/230; 436/504, 63, 94, 64, 804, 811, 813, 815 MM; 435/6, 172, 317, 91, 170, 270, 849

[56] References Cited

U.S. PATENT DOCUMENTS

| 4,139,346 | 2/1979 | Rabbani | 422/56 |
| 4,302,204 | 11/1981 | Wahl et al. | 23/230 B |
| 4,358,535 | 11/1982 | Falkow et al. | 435/5 |
| 4,359,535 | 11/1982 | Pieczenik | 435/317 |

FOREIGN PATENT DOCUMENTS 2034323 6/1980 United Kingdom .

OTHER PUBLICATIONS

Palukaitis, P. et al., Ann. Applied Biology, vol. 98, pp. 439–449, (1981).
Randles, J. W. et al., Phytopathology, vol. 70, pp. 185–189, (1980).
Owens, R. A. et al., Phytopathology, vol. 71(7), p. 770, (1981).
Semancik, J. S. et al., Phytopathology, vol. 68(9), pp. 1288–1292, (1978).
Owens, R. A. et al., Science, vol. 213(4508), pp. 670–672, (1981).
Wahl, G. M. et al., Proceedings National Academy of Sciences, vol. 76(8), pp. 3683–3687, (1979).
Owens, R. A. and Cress, D. E., Proceeding National Academy Sciences, vol. 77(9), pp. 5302–5306, (9–1980).
Dunn, A. R. et al., Cell, vol. 12, pp. 23–36, (1977).
Kafatos, F. C. et al., Nucleic Acids Research, vol. 7(6), pp. 1541–1552, (1979).
Moseley, S. L. et al., Journal of Infectious Diseases, vol. 142(6), pp. 892–898, (1980).
Dunn, A. R. et al., Methods in Enzymology, vol. 65(7), pp. 468–478, (1980).
Gillespie, D. et al., Journal of Molecular Biology, vol. 12(3), pp. 829–842, (1965).
Denhardt, D. T., Biochemical and Biophysical Research Communications, vol. 23(5), pp. 641–646, (1966).
Warnaar, S. O. et al., Biochemical and Biophysical Research Communications, vol. 24(4), pp. 554–558, (1966).
Grunstein, M. et al., Proceedings National Academy of Sciences, U.S.A., vol. 72(10), pp. 3961–3965, (1975).
Diener, T. O., Science, vol. 205, No. 4409, pp. 859–866, (1979), "Viroids: Structure and Function".
Zaitlin, M. et al., Virology, vol. 104, pp. 1–9, (7–1980).
Branch, A. D. and Dickson, E., Virology, vol. 104, pp. 10–26, (1980).
Owens, R. A., Virology, vol. 89, pp. 380–387, (1978).
Owens, R. A. et al., Virology, vol. 89, pp. 389–394, (1978).
Zeeten, G. A., et al. Virology, vol. 70, pp. 459–469, (1976).
Brandsma, J. and Miller, G., Proceedings National Academy Sciences, vol. 77, No. 11, pp. 6851–6855, (11–1980).
Owens, R. A. and Cress, D. E., Proceedings National Academy Sciences, vol. 77, No. 9, pp. 5302–5306, (9–1980).

*Primary Examiner*—Benjamin R. Padgett
*Assistant Examiner*—M. Moskowitz
*Attorney, Agent, or Firm*—M. Howard Silverstein; William E. Scott; David G. McConnell

[57] ABSTRACT

A rapid and sensitive method for diagnosing plant viroid diseases and viruses. Plant sap is bound to a solid support and the bound sample probed with a radioactively labelled DNA that is complementary to the viroid or to the nucleic acid of the virus being diagnosed. The radioactively labelled cDNA hybridizes with that viroid or virus RNA or DNA for which it is specific. DNA-RNA and DNA-DNA hybrids are detected by autoradiographic examination of the hybridized material.

6 Claims, No Drawings

SENSITIVE AND RAPID DIAGNOSIS OF VIROID DISEASES AND VIRUSES

BACKGROUND OF THE INVENTION

1. Field of the Invention

This invention relates to a method for diagnosing plant viroid diseases and more particularly to a method which is rapid and much more sensitive than any known method. The invention also relates to a method for diagnosing viruses.

2. Description of the Art

Currently available methods for diagnosing viroid diseases in plants and crops are time-consuming, inefficient, and not suitable for large scale screening operations. One method involves a bioassay on suitable host plant cultivars. However, this method requires extensive greenhouse space and is unreliable. Polyacrylamide gel electrophoresis of purified nucleic acid may also be used and although it required only 1 to 2 days to diagnose a viroid disease it is a laborious and expensive process. Polyacrylamide gel electrophoresis requires that the nucleic acid of interest, that is, deoxyribonucleic acid (DNA) or ribonucleic acid (RNA), be purified to remove interfering molecules.

SUMMARY OF THE INVENTION

An object of this invention is to provide a method of diagnosing viroid diseases that is suitable for large scale screening operations.

Another object is to provide a method for diagnosing viroid diseases that is many times more sensitive than currently available methods.

A further object is to provide a method which does not require the use of purified nucleic acid for the diagnosis of the viroid disease.

A still further object is to provide an accurate, sensitive and efficient method of diagnosing plant viroid disease in which the diagnosis is made from the plant sap rather than from purified nucleic acid.

Still another object is to provide a method for diagnosing plant viruses and for diagnosing plant viroid disease and plant viruses simultaneously.

In general, the above objects are accomplished by a method wherein a sample of plant sap or virus nucleic acid is bound to a solid support and the bound sample probed with a previously prepared and radioactively labelled DNA that is complementary (cDNA) to the viroid or to the nucleic acid of the virus being diagnosed. The radioactively labelled cDNA hybridizes with that viroid or virus RNA or DNA for which it is specific and which is present in the bound sample, and autoradiographic examination of the hybridized sample detects the presence of any DNA-RNA or DNA-DNA hybrids.

DESCRIPTION OF THE INVENTION

Plant viroid diseases and plant viruses are a potentially serious threat to agriculture throughout the world and particularly to plant producers and breeders. One of the problems encountered when dealing with these diseases is that the methods used to diagnose and detect them are very time-consuming and inefficient. Most of the tests used for detecting the presence of viroids or viruses in plants are within the scope of two categories, namely, bioassays which require inoculation of a variety of host plants and subsequent recording of symptoms and immunological techniques. The techniques of the latter category are dependent on the presence of protein in the pathogen and since viroids do not contain any protein, the immunological techniques are not directly applicable to their detection.

The invention will be described with particular reference to the diagnosis of potato spindle tuber viroid (PSTV) disease. Application of the method to viroid diseases of other plants would, in most cases, require the preparation of a radioactively labelled DNA that is complementary to the viroid being diagnosed. Known recombinant DNA techniques are used to make DNA that is complementary to the RNA or the DNA of the particular viroid. The recombinant DNA technology used to clone DNA complementary to the RNA of PSTV is described in Proc. Nat'l. Acad. Sci. U.S.A. 77, 5302–5306, 1980, as well as here and now.

PURIFICATION OF PSTV. The Beltsville strain of PSTV was purified from infected tomato tissue (*Lycopersicon esculentum* Mill., cv. Rutgers). Final purification involved two cycles of polyacrylamide gel electrophoresis and yielded an approximately equimolar mixture of circular and linear PSTV molecules.

SYNTHESIS OF DOUBLE-STRANDED cDNA. PSTV was treated with 0.025 unit of *Escherichia coli* alkaline phosphatase (electrophoretically purified,) per $\mu$g of RNA to remove 3'-terminal phosphate residues from linear molecules. Poly(A) was added by incubation with poly(A) polymerase (ATP: polynucleotide adenylyltransferase) from maize seedlings, and the polyadenylylated PSTV was recovered by phenol/chloroform extraction and ethanol precipitation.

Single-stranded PSTV cDNA was synthesized by incubating 6 $\mu$g of polyadenylylated PSTV with 114 units of reverse transcriptase in a 50-$\mu$l reaction mixture containing 10 mM Tris-HCl (pH 8.3), 50 mM KCl, 8 mM MgCl$_2$, 1 mM dithiothreitol, 0.04% Triton X-100 (octyl phenoxy polyethoxy ethanol, a nonionic detergent and emulsifier), p(dT)$_{12\text{-}18}$ at 1.4 A$_{260}$ unit/ml, and 1 mM each of dATP, dCTP, dGTP, and dTTP. After a 2-hr incubation at 37° C., the mixture was heated at 100° C. for 3 min, quenched at 0° C., and added to 50 $\mu$l of solution containing 180 mM potassium phosphate (pH 7.0), 10 mM MgCl$_2$, 20 mM dithiothreitol, 600 $\mu$M each of dATP, dCTP, dGTP, and dTTP, bovine serum albumin at 100 $\mu$g/ml, and 15 units of E. coli DNA polymerase 1. Second-strand DNA synthesis was allowed to proceed for 1 hr at 37° C. before the double-standed cDNA was recovered by ethanol precipitation. Non-base-paired regions were removed from the double-stranded PSTV cDNA by a 1-hr incubation at 37° C. with S1 nuclease at 200 units/ml in the presence of cucumber mosaic virus RNA carrier at 10 $\mu$g/ml double-stranded and 120 $\mu$g/ml single-stranded. S1-digested double-stranded PSTV cDNA was recovered by phenol/chloroform extraction and ethanol precipitation.

Single-stranded PSTV [$^{32}$P] cDNA was synthesized as described above except that the reaction mixture contained 60 $\mu$M dCTP [52 Ci/mmol (1 Ci = 3.7 $\times$ 10$^{10}$ becquerels)], and the cDNA synthesis reaction mixture was not heated before isolation of the cDNA by alkaline hydrolysis and ethanol precipitation.

CONSTRUCTION OF HYBRID PLASMIDS. Oligo(dG) and oligo(dC) tails were added to Pst 1-cleaved pBR322 plasmid DNA and S1-digested double-stranded PSTV cDNA, respectively, by incubation with calf thymus terminal deoxynucleotidyltransferase in the presence of 1 mM $Co^{2+}$. Oligo(dC)-tailed double-stranded PSTV cDNA and oligo(dG)-tailed pBR322 DNA were combined at a ratio of 1:10 (wt/wt), recovered by phenol/chloroform extraction and ethanol precipitation, and annealed before transformation.

TRANSFORMATION AND IDENTIFICATION OF RECOMBINANT CLONES. E. coli C600 ($r_k^- m_k^+$) was transformed by a modification of the $Mn^{2+}$, $Ca^{2+}$ transfection protocol described in J. Mol. Biol. 96, 495–509, 1975, under Pl-EKl containment conditions as required by the then current National Institutes of Health Guidelines for Recombinant DNA Research Tetracycline-resistant ampicillin-sensitive transformants were screened by a modified colony hybridization procedure using PSTV [$^{32}P$] cDNA as probe.

ISOLATION OF PLASMID DNA. Chloramphenicolamplified cultures were lysed with Triton X-100, and ribonuclease-treated cleared lysates were extracted with phenol/chloroform and precipitated with ethanol. Supercoiled DNA was isolated by two successive CsCl/ethidium bromide centrifugations.

ISOLATION, SIZING, AND CHARACTERIZATION OF CLONED DNAs. All DNA fragments were prepared and analyzed by electrophoresis in 5% polyacrylamide gels containing Tris/borate/EDTA buffer. DNA fragments were transferred to diazobenzyloxymethyl (DBM) paper before hybridization with PSTV [$^{32}P$] cDNA. Double-stranded restriction fragments were labeled at their 5' termini with [$\gamma$-$^{32}P$] ATP by using phage T4 polynucleotide kinase. Restriction endonuclease digestions were performed under the conditions recommended by the enzyme suppliers. Autoradiography was done with Kodak X-Omat film and Du Pont Cronex Lightning-Plus intensifying screens at $-70°$ C.

The potato spindle tuber disease is a potentially serious threat to seed potato producers, germplasm collections, and potato breeding programs. The disease is caused by a low molecular weight ($1.3 \times 10^5$) RNA, the potato spindle tuber viroid. PSTV is transmitted through vegetative propagation, foliar contact, and rue seed and pollen. Diagnosis of the disease is difficult because, at moderate temperatures, foliage symptoms often are indistinct or lacking, particularly in plants that have become infected during the current or most recent growing season. However, when tubers from such plants are used as seed potatoes, the viroid causes severe damage in the next succeeding years plants and may wipe out an entire crop, especially if plants are grown at high temperatures. Therefore, exclusion of PSTV from seed potatoes, especially those that are to be planted in subtropical or tropical climates is essential. However, such exclusion can only be accomplished by a method of detecting the viroid which is suitable for rapidly screening thousands of seed potato tubers. As noted above, presently available methods of detecting the viroid are not suitable for such screening purposes.

Using genetic engineering techniques, we have discovered and developed a test for detecting PSTV in potato seed and breeding stock. Briefly, we used recombinant DNA techniques to make DNA that was complementary to the RNA of the viroid, inserted the DNA into plasmids, but the plasmids back into *Escherichia coli* bacteria which reproduced the DNA complementary to the viroid. When purified and radioactively labelled, the cDNA provides a molecular probe to search for the viroid in host plants. In the method of this invention, crude tuber extract is spread across a nitrocellulose membrane, the membrane is baked to allow attachment of RNA, and the viroid cDNA is used as a hybridization probe. A distinct and unique advantage of the method of this invention is that is uses crude extracts instead of purified nucleic acid. In addition, following the same procedures used to diagnose PSTV, the method of this invention is applicable to the detection of viroids and viruses in other naturally occurring and genetically modified plants or crops.

The recombinant DNA technology for cloning DNA complementary to PSTV is essentially as follows: Viroid RNA is extracted from tomato leaves and separated from cellular RNA by gel electrophoresis; complementary DNA copies of the viroid are made using the enzyme reverse transcriptase; the single-stranded complementary DNA is converted to double-stranded DNA by the action of *E. coli* DNA polymerase I; the double-stranded complementary DNA is inserted into a plasmid (pBR-322) by recombinant DNA technology and introduced into laboratory cultures of the common bacterium *E. coli;* the *E. coli* bacteria reproduce and the plasmid DNA containing the PSTV-related sequences is also reproduced. The DNA complementary to PSTV is then purified and radioactively labeled. A large number of homogeneous, labeled DNA molecules are produced in this manner. These can be used as probes (or mirror images) to search for viroid RNA in host plants and also to learn how to prevent PSTV disease and other diseases caused by viroids.

The process of the invention is performed as follows:

Sap or extract is obtained by use of the extraction apparatus described by Gugerli, Revue Suisse Agric. 11(6): 253–260, 1979. Any other available automatic extraction apparatus would also be quite suitable. A 3 to 5 $\mu$l aliquot of the sap is applied to a nitrocellulose membrane supported in such a manner that the area to which sap is applied is not touching any solid object and the applied sap penetrates evenly into the membrane. Support is needed to prevent the applied sap from being drawn through the membrane by capillary action. A number of samples are applied to each membrane and are arranged in a grid with a space of about 1.0 cm between each sample. After samples have been applied the membrane is baked for about two hours at about 80° C. It is convenient but not necessary to do the baking in a vacuum oven at a reduced pressure. The amount by which the pressure is reduced is not critical. When the baking is completed the membranes are quite brittle so that care must be taken to prevent them from breaking apart. The nitrocellulose membranes are then processed, that is, they undergo hybridization with a nick-translated probe and are then subjected to autoradiography. The same aqueous buffer was used for both prehybridization (treatment prior to hybridization) and hybridization reactions and had the following composition: 40% formamide, 0.18M NaCl, 10.0 mM Na cacodylate; 1.0 mM ethylenediaminetetraacetic acid; 0.1% Na dodecylsulfate, and 400 $\mu$g/ml yeast transfer RNA (pH 7.0). Prehybridization and hybridization reactions were performed essentially as described in Proc. Natl. Acad. Sci. USA 76, 3683–3687, 1979. The principle differences were in the composition of solutions in which the reactions were conducted, and the times and temperatures of the reactions. Prehybridization was done at 42° C. for 16 hrs. in the presence of the above-noted buffer and 1.0% glycine and hybridization was done at 55° C. for 24 hrs. in the presence of the buffer, 10% dextran sulfate and $1–2.5 \times 10^6$ cpm/ml [32p] nick-translated pDC-29 recombinant DNA. Nick-translation in the presence of $[\alpha\text{-}^{32}p]dCTP$ (deoxycytidine 5'$[\alpha\text{-}^{32}p]$ triphosphate) followed the procedure described in J. Biol. Chem. 245 39–45, 1970, and yielded DNA with an initial specific activity of $\sim 2 \times 10^8$ cpm/μg. The ratio of buffer volume to membrane area was at least 1 ml/35 cm$^2$. Nick-translated DNA was denatured by heating for 2 min at 100° C. in the presence of 50% formamide before addition to the hybridization reaction. Nitrocellulose membranes were washed at room temperature with five changes of 0.36M NaCl-5 mM TRIS-HCl (pH 7.5)-0.1% sodium dodecylsulfate buffer and two changes of this buffer diluted ten-fold before autoradiography for 24–48 hrs. at −70° C. with a screen type X-ray film such as the Kodak X-Omat films and a calcium tungstate screen such as the DuPont Cronex Lightning-Plus intensifying screens.

At least one healthy and one known PSTV-infected sample are included as controls. As a matter of convenience we also spot identical samples on at least two membranes so that if the hybridization has to be repeated we will not have to prepare new sap samples.

If an automatic extraction apparatus is not available, sap or extract can be obtained by the following procedure: Buffer for homogenization of a leaf or etiolated sprout or other plant tissue to obtain the sap used for diagnosis is freshly prepared just prior to use by mixing the following constituents:

200 mM K$_2$HPO$_4$ 0.35 gm
10 mM sodium diethyldithiocarbamate 22.5 mg
5 mM dithiothreitol 7.7 mg
0.1% Triton X-100[1] 1.0 ml of 1.0% stock[2]
Add H$_2$O to make a final volume of 10.0 ml.
[1] Octylphenoxy polyethoxy ethanol [2] The 1.0% stock Triton X-100 solution is stored in a frozen state.

From 0.05 to 0.1 gm of leaf, sprout, or other plant tissue is homogenized with 0.1 to 0.2 ml of the freshly prepared buffer in a small conical ground glass homogenizer. Although it is not critical or essential, the homogenizer and the buffer containing plant tissue may be chilled prior to and during homogenization. Tissue debris, that is, any large particles of tissue, is removed by centrifuging for 2 to 3 minutes at top speed, about 4000 rpm in a clinical centrifuge. A 3 to 5 μl aliquot of the sap is then applied to a nitrocellulose membrane and the same procedure as described above followed.

Our autoradiographic data show that PSTV stably bind to diazobenzyloxymethyl (DBM) paper as well as to nitrocellulose membranes. However, we found that nitrocellulose membranes are simpler and less expensive to use and are, therefore, the preferred solid support for our method. Comparison of relative autoradiographic intensities showed that the presence of sap from uninfected tuber sprouts reduced the binding of PSTV approximately tenfold, but 83–250 pg of PSTV were still easily detected after hybridization with radioactive recombinant DNA. This amount is equivalent to a concentration of 0.04–0.125 μg PSTV/g tuber sprouts. Actively growing infected potato tissue contains $\geq 0.5$ μg PSTV/g tissue. Our hybridization method is therefore adequate to detect PSTV in potato tissue. The results also showed that the relatively high ionic strength and diethyldithiocarbamate concentration of the extraction buffer required to release PSTV from nuclei and inhibit enzymatic polyphenol oxidation did not interfere with PSTV binding to nitrocellulose.

The accuracy and reliability of the method of our invention were also demonstrated by the autoradiographic results. No reaction was detected with sap prepared from healthy (non-infected) tubers of six commercial varieties. Sap samples prepared from sprouts of individual PSTV-infected tubers of a given variety were found to contain similar concentrations of PSTV. In addition, all three portions of tuber tested, sprouts, axillary buds ("eyes"), and the epidermis between the axillary buds, contained detectable concentrations of PSTV ($\geq 0.08$ μg PSTV/g tissue). The data obtained from extensive experimentation demonstrate the feasibility of PSTV detection by the method of our invention. Although the entire screening procedure requires 4 days for completion, a large number of samples can be applied to each nitrocellulose membrane and several membranes can be hybridized simultaneously. As noted above, preparation of sap from the tuber tissue is simple. The method can be automated in much the same way that a sensitive method for the simultaneous detection of several important viruses in potato tubers has been automated, Revue Suisse Agric. 11,(6) 253–260, 1979. The sensitivity of our nucleic acid hybridization assay is equal to or greater than that of the ELISA (enzyme-linked immunosorbent assay) tests, J. Gen. Virol. 33, 165–167, 1976, used to detect potato viruses. Thus, potato tubers can be tested simultaneously for the presence of important viruses and for PSTV. The method of our invention is approximately ten times more sensitive than polyacrylamide gel electrophoresis.

The RNA-DNA hybrids formed in our procedure contain not only PSTV cDNA but also up to a ten-fold excess of unhybridized pBR322 vector DNA. The PSTV-specific insert of pDC-29, contains 460 base pairs, while the pBR322 vector contains 4361 base pairs. The use of dextran sulfate to accelerate the rate of nucleic acid hybridization causes additional amplification with double-stranded probes. The randomly cleaved, partially complementary probe fragments can form extensive networks both before and after the DNA sequences complementary to PSTV hybridize to the immobilized PSTV. We would expect a similar assay for PSTV which used single-stranded cDNA to be significantly less sensitive.

The method of this invention has been described mostly with reference to the detection of plant viroid disease. However, as noted, it is applicable to the detection of plant viruses in which case the particular virus involved is purified, the nucleic acid extracted and double-stranded DNA is prepared by the method described above for viroids. When the virus contains RNA, the cDNA is made using the enzyme reverse transcriptase as with the viroids. When the virus contains double-stranded DNA, the DNA is inserted directly into the pBR 322 plasmid; when it contains single-stranded DNA, the DNA is converted to double-stranded DNA by the action of E. coli DNA polymerase I. Cloning of the recombinant DNA is accomplished by the procedure described above for the viroids.

A major difference in use of the method for detecting viruses is the need to release nucleic acid from virus particles present in the sap or test sample. This is accomplished by use of certain detergents such as sodium dodecylsulfate or by phenol extraction of the plant tissue or by any other appropriate treatment. However, since the method of this invention is highly sensitive, the small amount of virus-specific nucleic acid occurring free in plant tissue may be sufficient for reliable detection of virus infection.

As noted above, our invention is unique in that it uses crude extracts instead of purified nucleic acid. It is also the first application of a membrane filter hybridization technique to the detection of an RNA pathogen.

We claim:

1. A method for diagnosing viroid diseases in plants, comprising:
   (a) obtaining sap from the plant being diagnosed;
   (b) binding the plant sap obtained in step (a) to a solid support;
   (c) probing the material bound to the solid support in step (b) with a previously prepared and radioactively labeled DNA that is complementary to the viroid RNA being diagnosed, said probing being done for the purpose of hybridizing any unpurified viroid-RNA or viroid DNA present in the bound plant sap; and
   (d) subjecting the probed material to autoradiographic examination to detect the presence of any DNA-RNA or DNA-DNA hybrids.

2. A method for diagnosing potato spindle tuber viroid disease in potato tubers comprising:
   (a) obtaining sap from the potato tuber being diagnosed;
   (b) binding the sap obtained in step (a) to a solid support;
   (c) probing the material bound to the solid support in step (b) with a previously prepared and radioactively labeled DNA that is complementary to PSTV nucleic acid the effect of said probing being the hybridization of any unpurified PSTV-RNA present in the bound material; and
   (d) subjecting the probed material to autoradiographic examination to detect the presence of any DNA-RNA hybrids.

3. The method of claim 2 in which an automatic extraction apparatus is used to obtain the sap.

4. The method of claim 3 in which the solid support is a nitrocellulose membrane.

5. The method of claim 4 in which the DNA complementary to PSTV-RNA is prepared by
   (a) extracting viroid RNA from tomato leaves;
   (b) separating the viroid RNA from cellular RNA;
   (c) treating the separated viroid RNA of step (b) with the enzyme reverse transcriptase to make complementary DNA copies of the viroid;
   (d) converting the single-stranded complementary DNA of step (c) to double-stranded DNA by the action of *E. coli* DNA polymerase I;
   (e) inserting the double-stranded complementary DNA into a pBR-322 plasmid;
   (f) introducing the recombined plasmid of step (e) into cultures of *E. coli* bacteria; and
   (g) allowing the *E. coli* bacteria to reproduce.

6. A method for diagnosing viruses in plants, comprising:
   (a) obtaining sap from the plant being diagnosed;
   (b) binding the sap obtained in step (a) to a solid support;
   (c) probing the material bound to the solid support in step (b) with a radioactively labelled DNA that is complementary to the nucleic acid of the virus being diagnosed to hybridize unpurified virus RNA and virus DNA for which the cDNA is specific; and
   (d) autoradiographically examining the hybridized virus RNA and DNA of step (c) to detect the presence of DNA-RNA and DNA-DNA hybrids.

* * * * *